US011000695B2

(12) United States Patent
Liang

(10) Patent No.: US 11,000,695 B2
(45) Date of Patent: May 11, 2021

(54) METHOD FOR TREATING MALE SEXUAL DYSFUNCTION BY USING UNDERPANTS COMPRISING FAR-INFRARED FIBERS

(71) Applicant: GREEN ENERGY NANO TECHNOLOGY CO., LTD., Taipei (TW)

(72) Inventor: Tien-Show Liang, Taipei (TW)

(73) Assignee: GREEN ENERGY NANO TECHNOLOGY CO., LTD., Taipei (TW)

( * ) Notice: Subject to any disclaimer, the term of this patent is extended or adjusted under 35 U.S.C. 154(b) by 0 days.

(21) Appl. No.: 16/562,349

(22) Filed: Sep. 5, 2019

(65) Prior Publication Data

US 2019/0388704 A1    Dec. 26, 2019

Related U.S. Application Data

(63) Continuation of application No. 15/709,516, filed on Sep. 20, 2017, now abandoned.

(51) Int. Cl.
*A61N 5/06* (2006.01)
*A41B 9/02* (2006.01)
(Continued)

(52) U.S. Cl.
CPC .............. *A61N 5/0613* (2013.01); *A41B 9/02* (2013.01); *A41B 17/00* (2013.01); *A61F 5/41* (2013.01);
(Continued)

(58) Field of Classification Search
CPC ............ A61N 5/0613; A61N 2005/063; A61N 2005/0645; A61N 2005/066;
(Continued)

(56) References Cited

U.S. PATENT DOCUMENTS 9,408,483 B2    8/2016  Liang
2004/0225049 A1  11/2004 Komuro
(Continued)

FOREIGN PATENT DOCUMENTS

JP        04-073226    *  3/1992   ............... A61N 5/06
JP        04073226 A     3/1992

*Primary Examiner* — Eric D. Bertram
(74) *Attorney, Agent, or Firm* — Anova Law Group, PLLC

(57) ABSTRACT

Differing from conventional approaches for improving sexual dysfunction of an adult man being commonly achieved by letting the adult man administer a dosage of synthetic drug or a composition of Chinese herbal medicines, the present invention particularly discloses a method for treating male sexual dysfunction by using underpants comprising far-infrared fibers. Clinical data have proved that, after wearing this underpants for 3 months, both the men diagnosed with sexual dysfunction and the men not sure to suffer from sexual dysfunction have an apparent progress on improvements of their erectile ability, erectile quality, ejaculation control ability, and lower urinary tract symptoms (LUTS). Moreover, clinical data have also proved that, despite the fact that a male person wears the underpants provided by the present invention for three months, there is no adverse effect induced by the underpants for causing the physiological condition of the men be abnormal.

8 Claims, 21 Drawing Sheets

(51) Int. Cl.
  *A41B 17/00* (2006.01)
  *G09B 3/10* (2006.01)
  *G09B 3/06* (2006.01)
  *A61F 5/41* (2006.01)

(52) U.S. Cl.
  CPC .............. *G09B 3/06* (2013.01); *G09B 3/10* (2013.01); *A41B 2400/32* (2013.01); *A41B 2500/20* (2013.01); *A61N 2005/063* (2013.01); *A61N 2005/066* (2013.01); *A61N 2005/0645* (2013.01)

(58) Field of Classification Search
  CPC ........ A41B 9/02–06; A41B 9/001–008; A41B 17/00; A41B 2400/32; A41B 2500/00–54; A61F 5/41
  See application file for complete search history.

(56) References Cited

U.S. PATENT DOCUMENTS

| | | |
|---|---|---|
| 2013/0117911 A1 | 5/2013 | Nam |
| 2016/0353818 A1 | 12/2016 | Psipsikas et al. |
| 2017/0135427 A1 | 5/2017 | Yeung |
| 2018/0127903 A1 | 5/2018 | Thatcher |
| 2018/0305520 A1 | 10/2018 | Yang |
| 2019/0009105 A1 | 1/2019 | Sheng et al. |
| 2019/0082747 A1* | 3/2019 | Liang .................. D01F 6/06 |

\* cited by examiner

| Questionnaire: IIEF-5 |||||||
|---|---|---|---|---|---|---|
| Over the past 6 months: |||||||
| 1. How do you rate your confidence that you could get and keep an erection? |||||||
| No confidence | Very low | low | Moderate | High | Very High ||
| 0 | 1 | 2 | 3 | 4 | 5 ||
| 2. When you had erections with sexual stimulation, how often were your erections hard enough for penetration? |||||||
| No sexuality | Never | A few times | Sometimes | Most times | Always ||
| 0 | 1 | 2 | 3 | 4 | 5 ||
| 3. During sexual intercourse, how often were you able to maintain your erection after you had penetrated your partner? |||||||
| No sexuality | Never | A few times | Sometimes | Most times | Always ||
| 0 | 1 | 2 | 3 | 4 | 5 ||
| 4. During sexual intercourse, how difficult was it to maintain your erection to completion of intercourse? |||||||
| No sexuality | Extremely difficult | Very difficult | Difficult | Slightly difficult | Not difficult ||
| 0 | 1 | 2 | 3 | 4 | 5 ||
| 5. When you attempted sexual intercourse, how often was it satisfactory for you? |||||||
| No sexuality | Never | A few times | Sometimes | Most times | Always ||
| 0 | 1 | 2 | 3 | 4 | 5 ||

Total score: _____

FIG. 7

| Quality of Erection Questionnaire (QEQ) |
|---|
| 1. You had erections hard enough for penetration of your partner: |
| Never    A few times    Sometimes    Most times    Always<br>1    2    3    4    5 |
| 2. Your ability to keep your erection to completion of sexual intercourse was: |
| Very unsatisfactory    Somewhat unsatisfactory    Neither satisfactory nor unsatisfactory    Somewhat satisfactory    Very satisfactory<br>1    2    3    4    1 |
| 3. The length of time (from when you started sexual activity) until your erection was hard enough to participate in sexual intercourse was: |
| Very unsatisfactory    Somewhat unsatisfactory    Neither satisfactory nor unsatisfactory    Somewhat satisfactory    Very satisfactory<br>1    2    3    4    1 |
| 4. The hardness of your erection was: |
| Very unsatisfactory    Somewhat unsatisfactory    Neither satisfactory nor unsatisfactory    Somewhat satisfactory    Very satisfactory<br>1    2    3    4    1 |
| 5. The overall quality of your erection was: |
| Very unsatisfactory    Somewhat unsatisfactory    Neither satisfactory nor unsatisfactory    Somewhat satisfactory    Very satisfactory<br>1    2    3    4    1 |

Total score: _____

FIG. 8

| Premature Ejaculation Diagnostic Tool (PEDT) | | | | |
|---|---|---|---|---|
| 1. How difficult is it for you to delay ejaculation? | | | | |
| Not difficult at all | Somewhat difficult | Moderately difficult | Very difficult | Extremely difficult |
| 0 | 1 | 2 | 3 | 4 |
| 2. Do you ejaculate before you want to? | | | | |
| Never or almost never (0%) | Less than half the time (25%) | About half the time (50%) | Over half The time (75%) | Always or almost always (100%) |
| 0 | 1 | 2 | 3 | 4 |
| 3. Do you ejaculate with very little stimulation? | | | | |
| Never or almost never (0%) | Less than half the time (25%) | About half the time (50%) | Over half The time (75%) | Always or almost always (100%) |
| 0 | 1 | 2 | 3 | 4 |
| 4. Do you feel frustrated because of ejaculating before you want to? | | | | |
| Not at all | Slightly | Moderately | Very | Extremely |
| 0 | 1 | 2 | 3 | 4 |
| 5. How concerned are you that your time to ejaculation leaves your partner unfulfilled? | | | | |
| Not at all | Slightly | Moderately | Very | Extremely |
| 0 | 1 | 2 | 3 | 4 |

FIG. 9

Questionnaire of IPSS

| In the past month: | Not at All | Less than 1 in 5 Times | Less than Half the Time | About Half the Time | More than Half the Time | Almost Always | Your score |
|---|---|---|---|---|---|---|---|
| 1. Incomplete Emptying<br>How often have you had the sensation of not emptying your bladder? | 0 | 1 | 2 | 3 | 4 | 5 | |
| 2. Frequency<br>How often have you had to urinate less than every two hours? | 0 | 1 | 2 | 3 | 4 | 5 | |
| 3. Intermittency<br>How often have you found you stopped and started again several times when you urinated? | 0 | 1 | 2 | 3 | 4 | 5 | |
| 4. Urgency<br>How often have you found it difficult to postpone urination? | 0 | 1 | 2 | 3 | 4 | 5 | |
| 5. Weak Stream<br>How often have you had a weak urinary stream? | 0 | 1 | 2 | 3 | 4 | 5 | |
| 6. Straining<br>How often have you had to strain to start urination? | 0 | 1 | 2 | 3 | 4 | 5 | |
| | None | 1 Time | 2 Times | 3 Times | 4 Times | 5 Times | |
| 7. Nocturia<br>How many times did you typically get up at night to urinate? | 0 | 1 | 2 | 3 | 4 | 5 | |
| Total I-PSS Score | | | | | | | |

FIG. 10

METHOD FOR TREATING MALE SEXUAL DYSFUNCTION BY USING UNDERPANTS COMPRISING FAR-INFRARED FIBERS

CROSS-REFERENCE TO RELATED APPLICATIONS

This application is a continuation application of U.S. patent application Ser. No. 15/709,516 filed on Sep. 20, 2017 entitled "METHOD FOR TREATING MALE SEXUAL DYSFUNCTION BY USING UNDERPANTS COMPRISING FAR-INFRARED FIBERS".

BACKGROUND OF THE INVENTION

1. Field of the Invention

The present invention relates to the technology field of far-infrared fibers, and more particularly to a method for treating male sexual dysfunction by using underpants comprising far-infrared fibers.

2. Description of the Prior Art

Male sexual dysfunction includes erectile dysfunction (ED), premature ejaculation (PE), delayed ejaculation, and low libido, wherein mental factors, physiological factors and drug factors are known able to cause the male sexual dysfunction. Moreover, clinical research reports that mental factor may formed by melancholia, low self-confidence, and anxiety of sexual performance, and the physiological factor is commonly resulted from cardiovascular diseases, endocrine system diseases and disorders, or injury or fracture of penile corpus cavernosum.

Statistical data indicate that, about half of all men between the ages of 40 and 70 suffer from erectile dysfunction (ED) to some degree. ED is one of the most common chronic diseases affecting men and its prevalence increases with aging. Phosphodiesterase-5 inhibitors (PDE5-I) are commonly used for on-demand or chronic treatment of ED. Viagra (sildenafil), Levitra (vardenafil) and Cialis (tadalafil) are currently known prescription ED drugs comprising PDE5-I. By dilating blood vessels and relaxing smooth muscle tissues in penis, these drugs successfully improve or treat erectile dysfunction. However, this is the result of a series of conditions occurring simultaneously. When ED drug is taken correctly, it is no longer a concern. Nevertheless, in the mind of the public, use of the ED drug is at this time invariably considered dangerous for patients with heart disease. Moreover, it is well known that these ED drugs may cause unwanted side effects that require medical attention.

In view of the fact that most of ED drugs induce unwanted side effects, U.S. Pat. No. 7,147,874 discloses a pharmaceutical composition for prevention and treatment of premature ejaculation. The pharmaceutical composition comprises an extract of *Bufonis Venenuin* and an extract of Ginseng. To carry out treatment of premature ejaculation, 0.2 g of gel pharmaceutical composition is applied to an adult man's penis glans, such that the contraction of penile smooth muscle is reduced so as to extend erection time of the adult man. However, the pharmaceutical composition is just used to prevent men from premature ejaculation during his sexual intercourse, but fail to provide a real improvement on solving sexual dysfunction to the men.

Accordingly, U.S. Pat. No. 8,211,006 discloses a penis erection stabilizer. FIG. 1 shows a stereo diagram of the penis erection stabilizer. From FIG. 1, it is understood that the penis erection stabilizer 1' comprises a stabilizer body 11' and a through-hole 12' defined through a center portion of the stabilizer body 11'. It is well know that, the blood supplied to the spongy tissue of an adult man's penis would flow back via vein when the adult man ejaculates or loses tension due to fatigue under sexual intercourse. In the meantime, because the adult man's penis is sleeved with the penis erection stabilizer 1', the blood in the expanded penis should first pass through a small diameter portion of the through-hole 12', such that the small diameter portion keeps the blood so as to retard the discharge of the blood. Eventually, the erected state of the penis can be maintained for a time sufficient for the completion of the sexual intercourse. It is worth noting that, owing to the fact that the use way of the penis erection stabilizer 1' is to sleeve on user's penis, it is presumably that frequently-repeating use of the penis erection stabilizer 1' would cause the injury of the penis.

From above descriptions, it is clear that both the pharmaceutical composition for prevention of premature ejaculation and the penis erection stabilizer 1' show practical-application drawbacks. In view of that, inventors of the present application have made great efforts to make inventive research thereon and eventually provided a method for treating male sexual dysfunction by using underpants comprising far-infrared fibers.

SUMMARY OF THE INVENTION

Differing from the fact that conventional approaches for improving sexual dysfunction of an adult man are commonly carried out by letting the adult man administer a dosage of synthetic drug or a composition of Chinese herbal medicines, the present invention particularly discloses a method for treating male sexual dysfunction by using underpants comprising far-infrared fibers. A variety of clinical data have proved that, after wearing this underpants for 3 months, both the men diagnosed with sexual dysfunction and the men not sure to suffer from sexual dysfunction have an apparent progress on improvements of their erectile ability, erectile quality, ejaculation control ability, and lower urinary tract symptoms (LUTS). Moreover, clinical data have also proved that, despite the fact that a male person wears the underpants provided by the present invention for three months, there is no any adverse effect induced by the underpants so as to cause the physiological condition of the men be abnormal.

In order to achieve the primary objective of the present invention, the inventor of the present invention provides an embodiment of the method for treating male sexual dysfunction by using underpants, comprising following steps:

(1) providing an underpants weaved from a plurality of far-infrared fibers and a plurality of fibers, wherein each of the far-infrared fibers comprises a polymer sheath and far-infrared metal powders doped in or enclosed by the polymer sheath; moreover, the far-infrared fibers having a fiber amount occupying 40-60 percent of a total fiber amount of the underpants; and (2) letting adult men diagnosed with sexual dysfunction or not sure to suffer from sexual dysfunction wear the underpants for at least one month.

Moreover, for achieving the primary objective of the present invention, the inventor of the present invention further provides another one embodiment of the method for treating male sexual dysfunction by using underpants, comprising following steps:

(1) providing an underpants weaved from a plurality of far-infrared fibers, wherein each of the far-infrared fibers comprises a polymer sheath and far-infrared powders doped in or enclosed by the polymer sheath; and (2) letting adult men diagnosed with sexual dysfunction or not sure to suffer from sexual dysfunction wear the underpants for at least one month.

In the two embodiments of the method, wherein the type of the underpants is selected from the group consisting of briefs, boxer briefs and boxer shorts.

In the two embodiments of the method, wherein the far-infrared powders comprises powdered titanium (Ti) with a first metal weight percent of 11-18 wt %, powdered germanium (Ge) with a second metal weight percent of 0.1-0.2 wt % and powdered zinc (Zn) with a third metal weight percent of 0.05-0.15 wt %.

In the two embodiments of the method, wherein the far-infrared fibers are able to emit a far-infrared ray with a wavelength in a range from 2 and the emissivity of the far-infrared ray is above 90%.

In the two embodiments of the method, wherein the far-infrared powders further comprises powdered oxide and powdered carbide for increasing the emissivity of the far-infrared ray.

In the two embodiments of the method, wherein the far-infrared powders further comprises other powdered metal selected from the group consisting of powdered copper (Cu), powdered silver (Ag), powdered aluminum (Al), powdered magnesium (Mg), a mixture made by any two or more aforesaid materials.

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein:

FIG. 7 shows a diagram for introducing an IIEF-5 questionnaire;

FIG. 8 shows a diagram for introducing a QEQ questionnaire;

FIG. 9 shows a diagram for introducing a PEDT questionnaire;

FIG. 10 shows a diagram for introducing an IPSS questionnaire;

DETAILED DESCRIPTION OF THE PREFERRED EMBODIMENTS

To more clearly describe a method for treating male sexual dysfunction by using underpants comprising far-infrared fibers according to the present invention, embodiments of the present invention will be described in detail with reference to the attached drawings hereinafter.

First Embodiment

Figure 1:
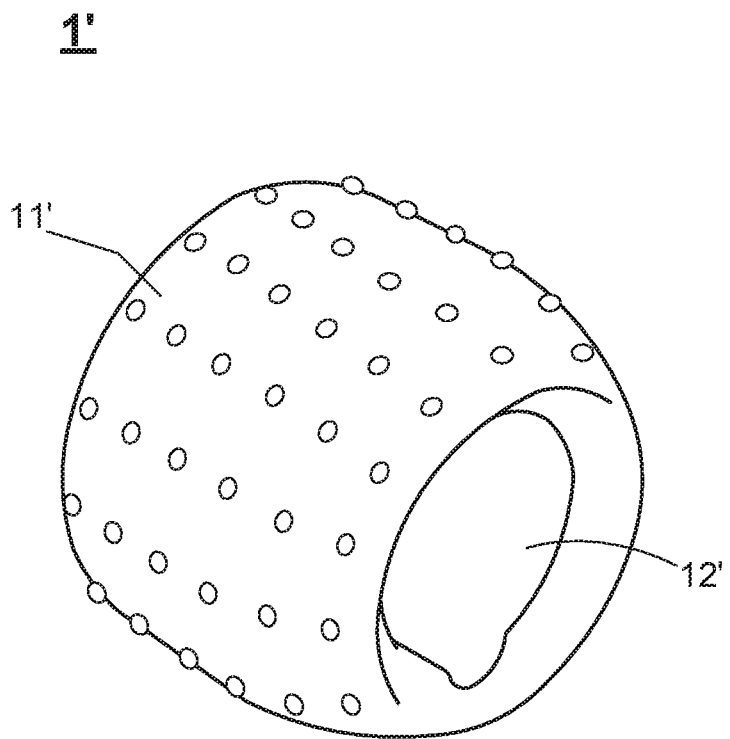
FIG. 1 shows a stereo diagram of a penis erection stabilizer.
Figure 2A:
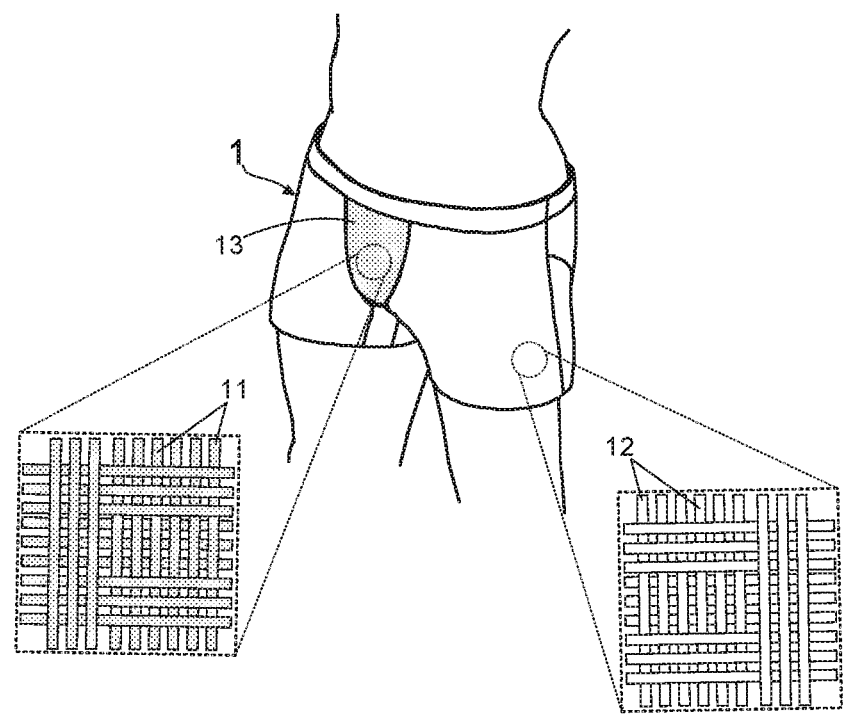
FIG. 2A and FIG. 2B show stereo diagrams of a first embodiment of an underpants capable of improving male sexual dysfunction.
Figure 2B:
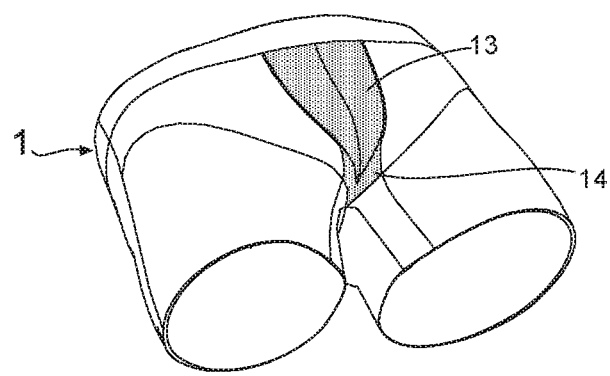

The inventors of the present invention find that the underpants comprising far-infrared fibers has a particular function to improve male sexual dysfunction. Please refer to FIG. 2A and FIG. 2B, where stereo diagrams of a first embodiment of an underpants capable of improving male sexual dysfunction are provided. According to FIG. 2A and FIG. 2B, it is understood that the underpants 1 capable of improving male sexual dysfunction is weaved from a plurality of far-infrared fibers 11 and a plurality of fibers 12, wherein the far-infrared fibers 11 has a fiber amount occupying 20-50 percent of a total fiber amount of the underpants 1. For instance, FIG. 2A and FIG. 2B indicate that the front rise portion 13 and the crotch portion 14 of the underpants 1 is constituted by the far-infrared fibers 11, and other portions of the underpants 1 is weaved from the fibers 12.

Figure 3:
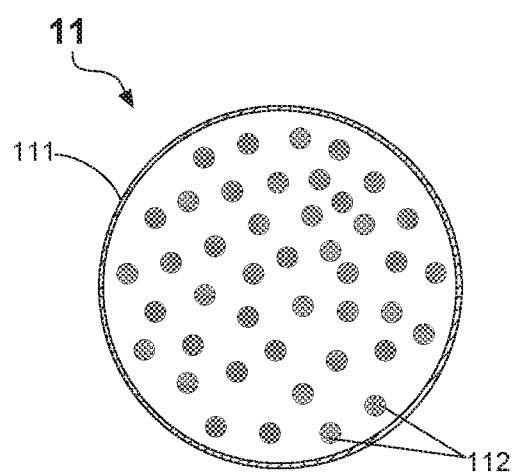
FIG. 3 shows a cross-sectional view of one far-infrared fiber.

FIG. 3 shows a cross-sectional view of one far-infrared fiber. In the present invention, the far-infrared fiber 11 comprises a polymer sheath 111 and far-infrared powders 112 doped in or enclosed by the polymer sheath 111. Moreover, the manufacturing material of the polymer sheath 111 is selected from the group consisting of polyester (PET), polyurethane (PU), Poly(vinyl chloride) (PVC), poly propylene (PP), and polyamide (PA). It is worth explaining that, vinyl contains phthalate chemicals or similar plasticizers that are used to turn hard polyvinyl chloride (PVC) into soft and pliable vinyl. Related research reports that phthalates are animal carcinogens and can cause fetal death, malformations, and reproductive toxicity in laboratory animals. Based on the reasons, the polymer sheath 11 can also be made of a polymer compound comprising silica of at least 50 wt %, wherein the chemical structure of the polymer compound is presented by following chemical formula 1.

[chemical formula 1]

In chemical formula 1, n is an integer in a range from 50 to 100. On the other hand, the far-infrared powders comprises powdered titanium (Ti) with a first metal weight percent of 11-18 wt %, powdered germanium (Ge) with a second metal weight percent of 0.1-0.2 wt % and powdered zinc (Zn) with a third metal weight percent of 0.05-0.15 wt %. By such arrangement, when an adult man wear this underpants 1, the far-infrared ray emitted from the front rise portion 13 and the crotch portion 14 of the underpants 1 would make the dilation of penile arteries of the adult man, and simultaneously urge blood to flow into the penile arteries so as to make the erection of the adult man's penis.

It needs further explain that, the far-infrared powders 112 further comprises powdered oxide and powdered carbide for increasing the emissivity of the far-infrared ray of the far-infrared fibers 11, wherein the powdered oxide is selected from the group consisting of: $Al_2O_3$, MgO, $NiO_2$, $SiO_2$, $ZrO_2$, and a mixture made by any two or more aforesaid materials. Moreover, the powdered carbide is selected from the group consisting of: TaC, ZrC, SiC, and a mixture made by any two or more aforesaid materials. By such arrangement, the front rise portion 13 and the crotch portion 14 of the underpants 1 are able to emit the far-infrared ray having an emissivity greater than 90% and a wavelength of 2-22 μm. In addition, other powdered metal such as powdered copper (Cu), powdered silver (Ag), powdered aluminum (Al), or powdered magnesium (Mg) can also be mixed into the far-infrared powders 112.

Figure 4A:
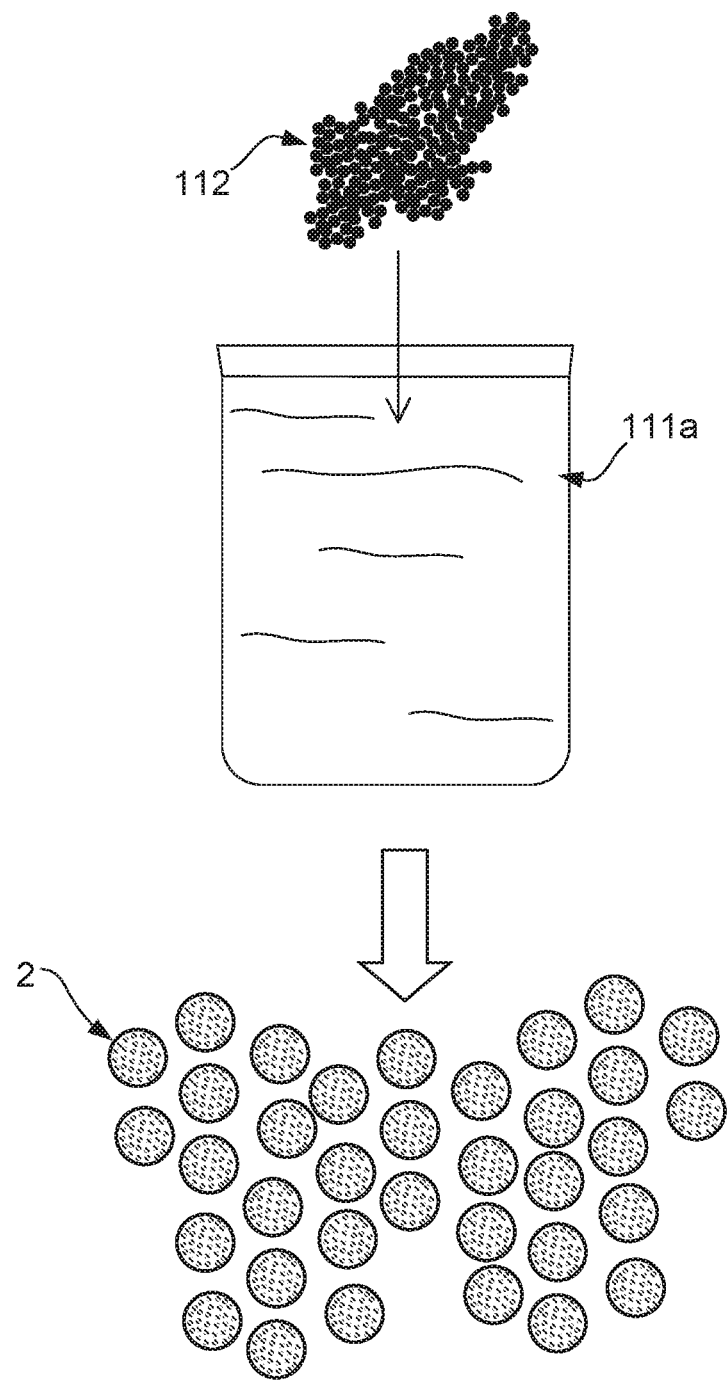
FIG. 4A, FIG. 4B and FIG. 4C show a schematic production processing flow of the underpants capable of improving male sexual dysfunction.
Figure 4B:
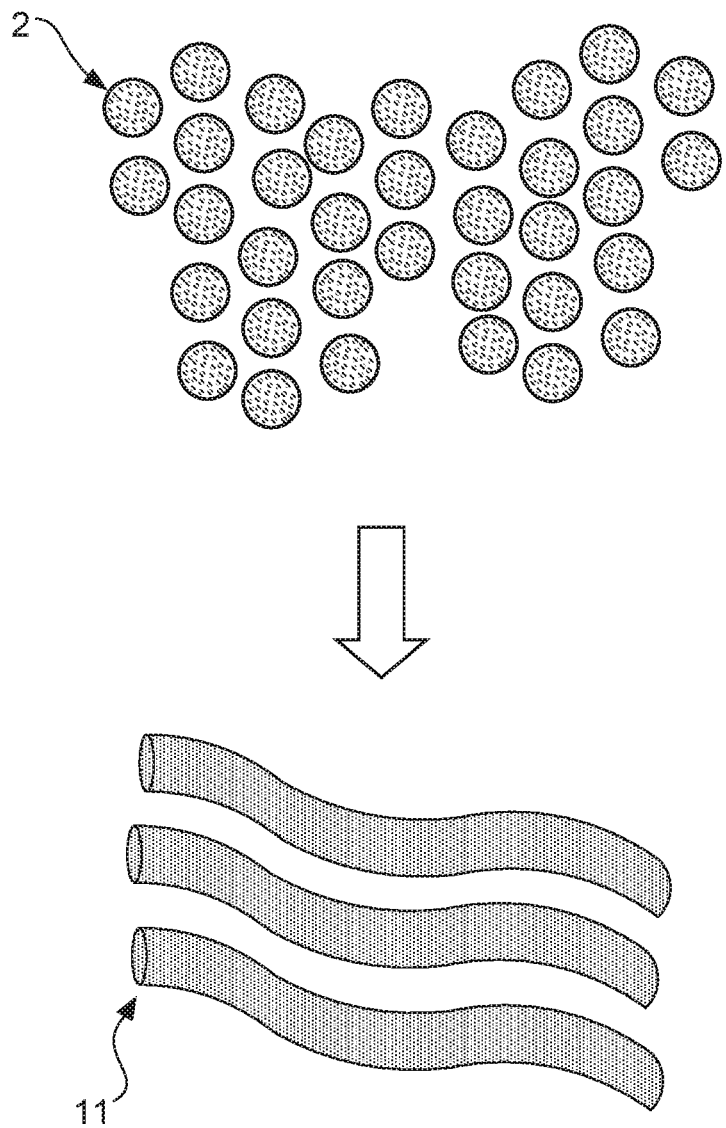
Figure 4C:
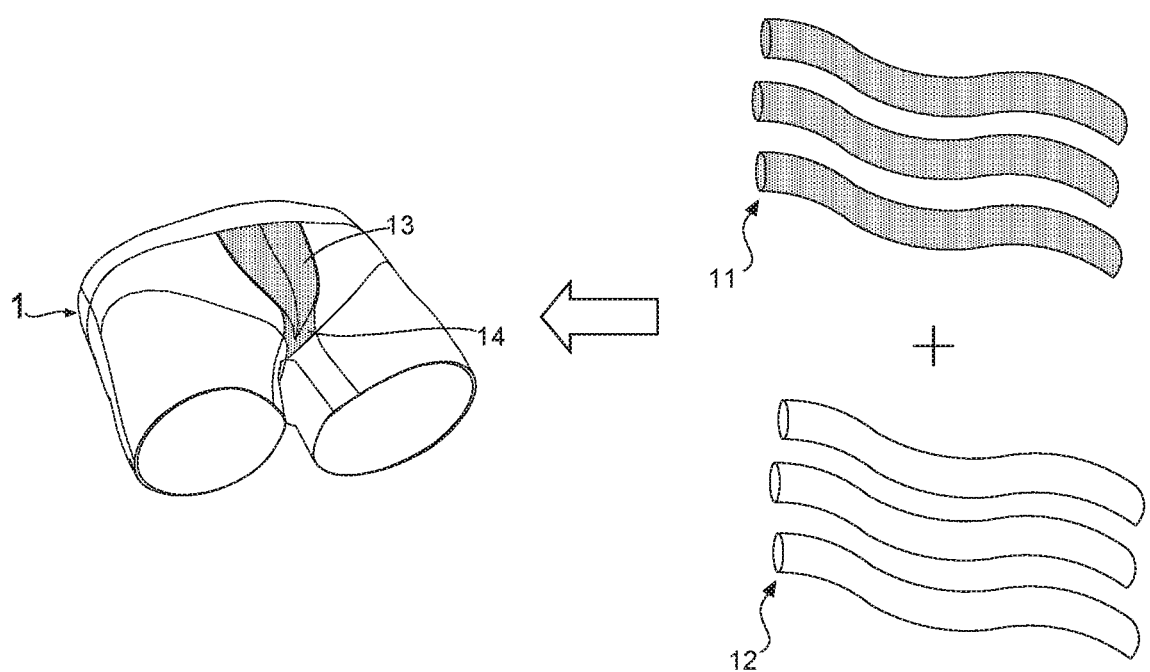

FIG. 4A, FIG. 4B and FIG. 4C show a schematic production processing flow of the underpants capable of improving male sexual dysfunction. The underpants 1 capable of improving male sexual dysfunction is manufactured through following process flow:

step (1): as FIG. 4A shows, to add far-infrared powders 112 into a polymer solution 111a, and then convert the polymer solution 111a to a plurality of masterbatches 2 through polymerization and granulation process;

step (2): as FIG. 4B shows, executing a spinning process for drawing the masterbatches 2 to a plurality of far-infrared fibers 11; and step (3): as FIG. 4C shows, the underpants 1 capable of improving male sexual dysfunction is weaved from the far-infrared fibers 11 and a plurality of fibers 12.

Second Embodiment

Figure 5:
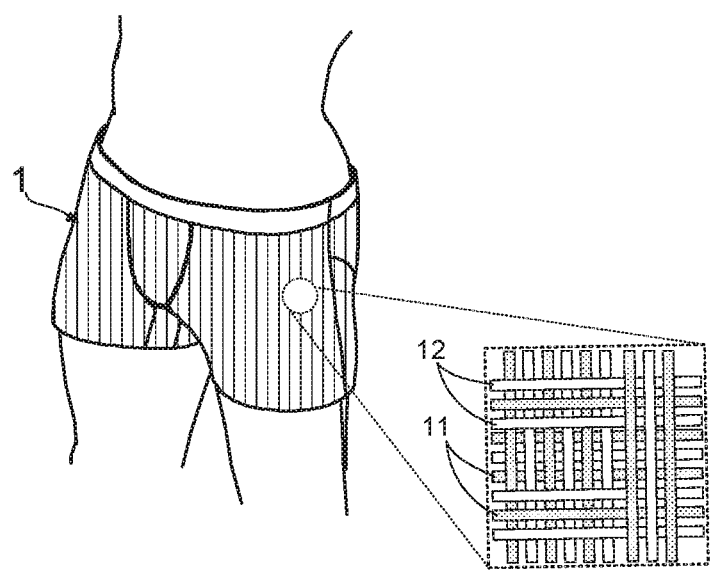
FIG. 5 shows a stereo diagram of a second embodiment of the underpants capable of improving male sexual dysfunction.

It needs to emphasize that, in spite of the fact that the fiber content of the far-infrared fibers 11 of the underpants 1 is in a range from 20% to 50%, that does not used for limiting the constitution of the underpants 1. In the first embodiment, what is weaved from the far-infrared fibers 11 are only the front rise portion 13 and the crotch portion 14 of the underpants 1, with the purpose of cost saving. Please refer to FIG. 5, which illustrates a stereo diagram of a second embodiment of the underpants capable of improving male sexual dysfunction. After comparing FIG. 2B with FIG. 5, it is found that the underpants 1 shown in FIG. 5 is a blend fabric of the far-infrared fibers 11 and the fibers 12, wherein the far-infrared fibers 11 has a maximum fiber amount occupying 50 percent of a total fiber amount of the underpants 1. However, for business benefit consideration, the far-infrared fibers 11 content of the underpants 1 must be limited to lower than 50% because the cost of the far-infrared fibers 11 is higher than the general fibers' 12.

Third Embodiment

Figure 6:
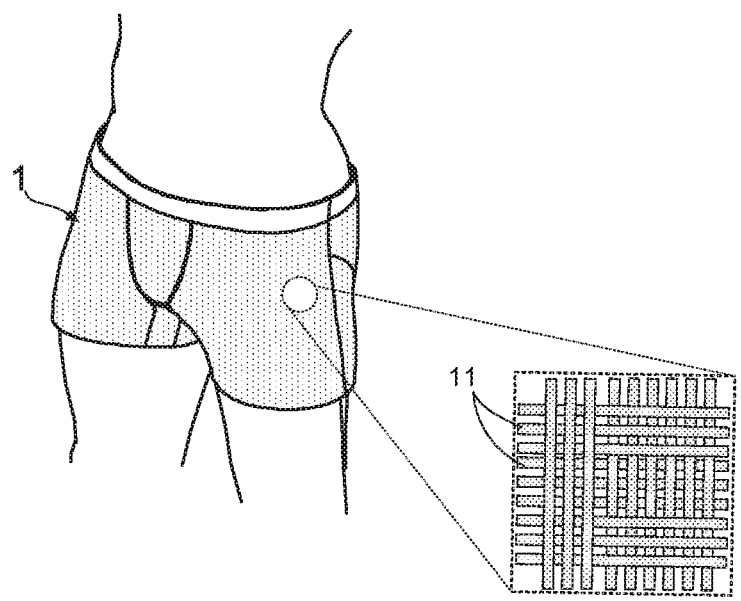
FIG. 6 shows a stereo diagram of a third embodiment of the underpants capable of improving male sexual dysfunction.

Of course, the far-infrared fibers 11 content of the underpants 1 may be greater than 50% without the consideration of business benefit. FIG. 6 shows a stereo diagram of a third embodiment of the underpants capable of improving male sexual dysfunction. Compared FIG. 5 with FIG. It is understood that the underpants 1 shown in FIG. 6 is weaved merely from the far-infrared fibers 11, such that the far-infrared fibers 11 content of the underpants 1 is 100%.

First Clinical Trials

A clinical trial is, essentially, any form of planned experiment that involves patients and is designed to elucidate the most effective treatment for patients with the underpants 1 weaved from the far-infrared fibers 11 and the fibers 12. More particularly, first clinical trials are typically utilized to evaluate the effectiveness of the underpants 1 on improving sexual dysfunction of adult men. According to following Table (1), adult men diagnosed with sexual dysfunction are chosen as test subjects, and further divided into control group (abbreviated to group C) and experimental group (abbreviated to group E) for completing 3-month clinical trials. It needs to further explain that, both the adult men of the group C and the group E wear the underpants 1 provided by the present invention. Moreover, the primary difference between the group C and the group E is that the adult men of the group C has been informed that the underpants they wore is a commercial underpants. On the other hand, in Table (1), physiology examination reports to be "abnormal" means the adult men suffer from hypertension.

TABLE (1)

| | Physiology examination | | Age | | | BMI | | |
|---|---|---|---|---|---|---|---|---|
| | Normal | Abnormal | Average | ± | Standard deviation | Normal | Over weight | Obese |
| Group C (n = 4) | 3 | 1 | 49 | ± | 8.18 | 2 | 2 | 0 |
| Group E (n = 5) | 4 | 1 | 47 | ± | 6.45 | 2 | 3 | 0 |

What is needed to emphasize is that the adult men are chosen as the test subjects after passing the following exclusion criteria:

(1) ever using sex hormone agents or PDE-5 inhibitors like Sildenafil, Vardenafil, or Tadalafil administered in the 7 days previously for the treatment of male sexual dysfunction;

(2) a long user of antihypertensive drugs, antidepressants, sedatives, anti-androgens, or medicines for treating peptic ulcer;

(3) ever being subject to serious injuries of central system, for example, stroke or spinal cord injury;

(4) ever suffering from erectile disorder caused by non-vascular diseases factors, such as nervous factors or hormone factors;
(5) being an HIV patient or the patient with liver disease;
(6) diagnosis of urethral stricture, urinary tract infection, prostatitis, prostate cancer, or bladder cancer;
(7) sexual partner is pregnant or in a breast-feeding period;
(8) being a patient with Peyronie's disease;
(9) suffering from alcoholism or tobacco addiction;
(10) suffering from cancer of prostate gland or other malignant neoplasms;
(11) will have an operation (surgical treatment) during clinical trials period;
(12) having an unhealthy mental status which will affect evaluations of clinical trials;
(13) ever completing at least one sexual performance test which will affect evaluations of clinical trials; and
(14) being ineligibility for the current study judged by investigators.

During 3-month clinical trials, the test subjects are requested to come back for follow up at the hospital every 1 month for completing the filling of four questionnaires of IIEF-5, QEQ, PEDT, and IPSS. Moreover, physiological data of the test subjects are also measured and recorded by nursing personnel. Diagrams of IIEF-5 questionnaire, QEQ questionnaire, PEDT questionnaire, and IPSS questionnaire are displayed in FIG. 7, FIG. 8, FIG. 9, and FIG. 10, respectively.

Figure 11:
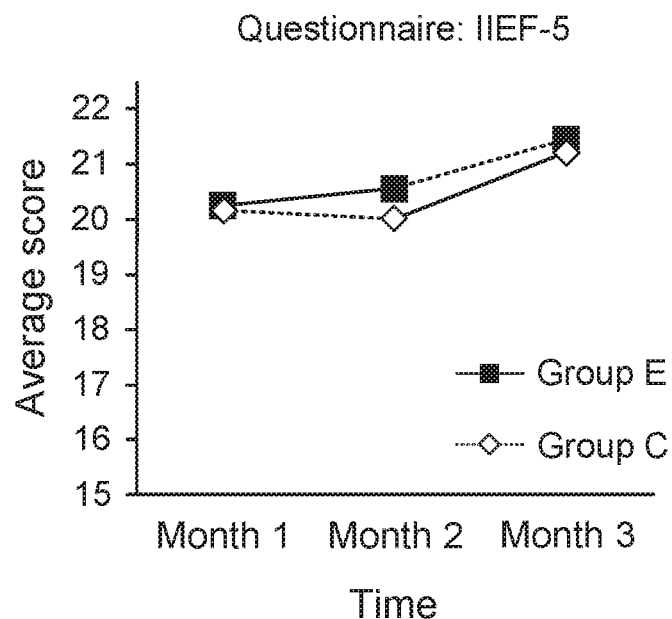
FIG. 11 shows a data graph of time of clinical experiment versus average score of questionnaire.
Figure 12:
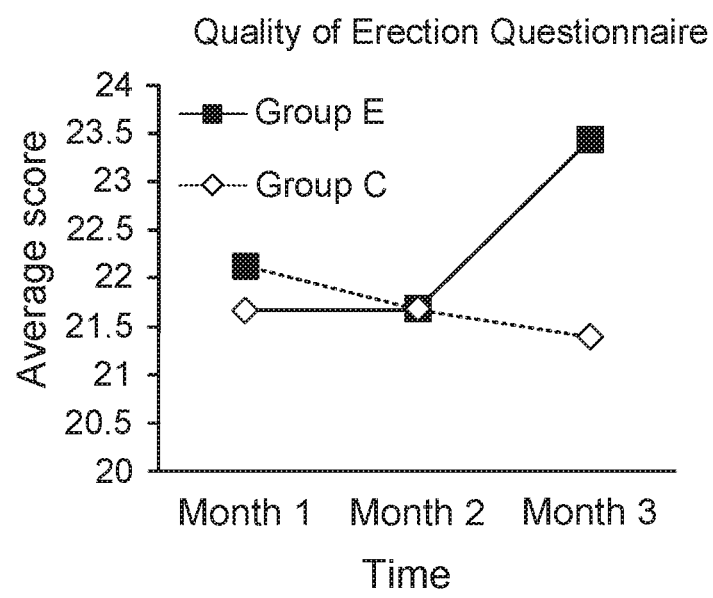
FIG. 12 shows a data graph of time of clinical experiment versus average score of questionnaire.
Figure 13:
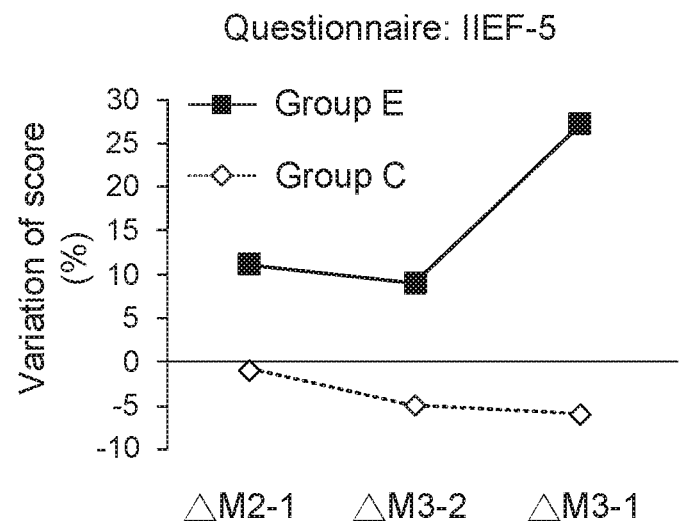
FIG. 13 shows a data graph for describing questionnaire score variation between adjacent two months.
Figure 14:
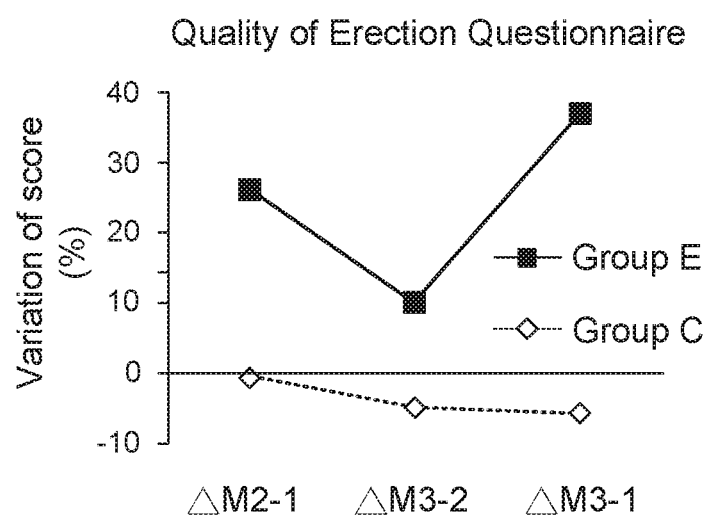
FIG. 14 shows a data graph for describing questionnaire score variation between adjacent two months.

Moreover, FIG. 11 shows a data graph of time of clinical experiment versus average score of questionnaire, and FIG. 12 shows a data graph of time of clinical experiment versus average score of questionnaire. From the data of clinical trials provided in FIG. 11 and FIG. 12, it is found that, compared to the adult men wearing the underpants provided by the present invention for one month, the adult men wearing the underpants provided by the present invention for three months have an apparent progress on improvements of their erectile ability and erectile quality. On the other hand, FIG. 13 shows a data graph for describing questionnaire score variation between adjacent two months and FIG. 14 shows a data graph for describing questionnaire score variation between adjacent two months. From the data of clinical trials provided in FIG. 13 and FIG. 14, it is further understood that, the adult men wearing the underpants provided by the present invention for three months have an apparent progress on improvements of their erectile ability and erectile quality, compared to the adult men wearing the underpants provided by the present invention for one month.

Figure 15:
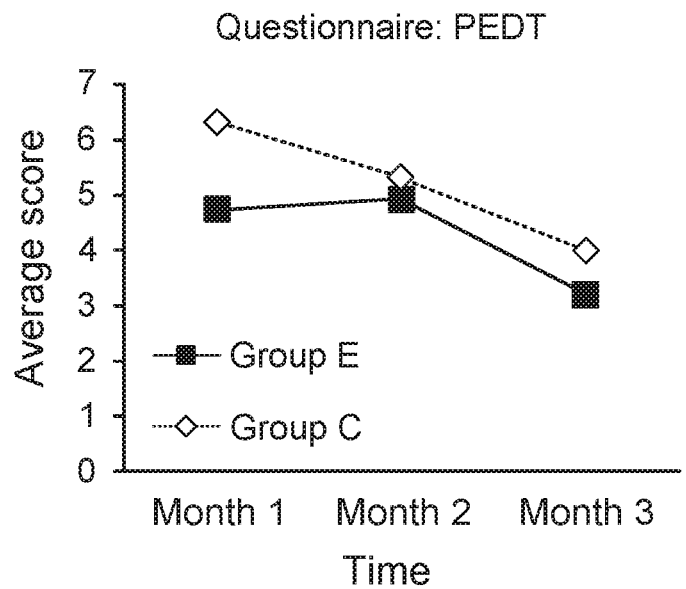
FIG. 15 shows a data graph of time of clinical experiment versus average score of questionnaire.
Figure 16:
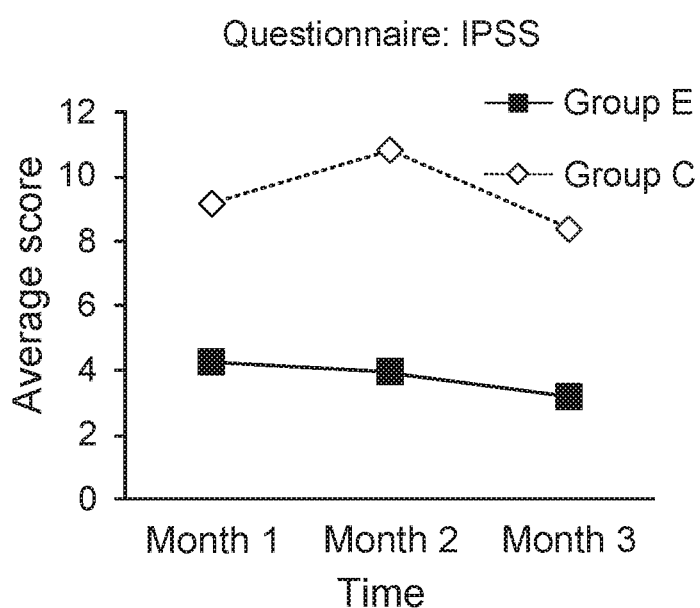
FIG. 16 shows a data graph of time of clinical experiment versus average score of questionnaire.
Figure 17:
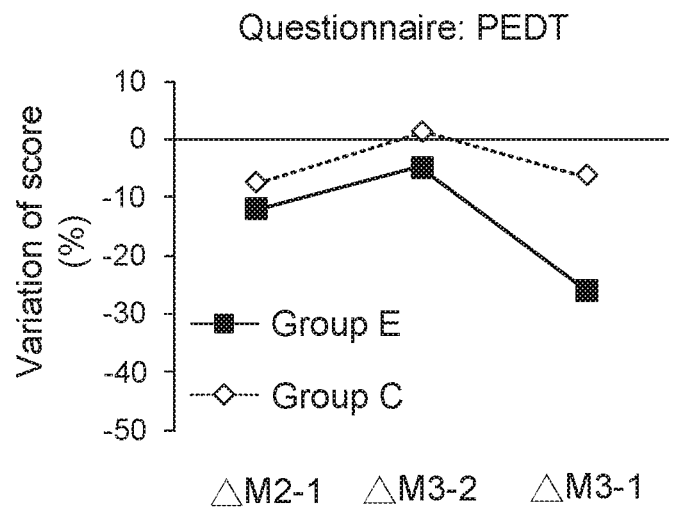
FIG. 17 shows a data graph for describing questionnaire score variation between adjacent two months.
Figure 18:
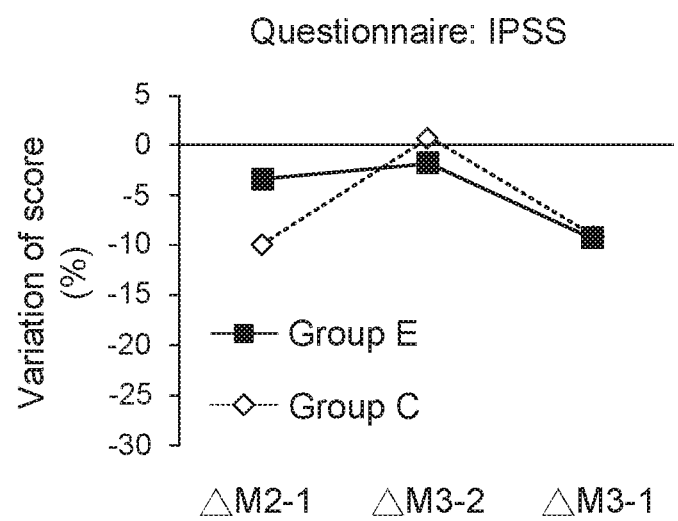
FIG. 18 shows a data graph for describing questionnaire score variation between adjacent two months.

In addition, FIG. 15 shows a data graph of time of clinical experiment versus average score of questionnaire, and FIG. 16 shows a data graph of time of clinical experiment versus average score of questionnaire. From the data of clinical trials provided in FIG. 15 and FIG. 16, it is found that, compared to the adult men wearing the underpants provided by the present invention for one month, the adult men wearing the underpants provided by the present invention for three months have an apparent progress on improvements of their ejaculation control ability and lower urinary tract symptoms (LUTS). On the other hand, FIG. 17 shows a data graph for describing questionnaire score variation between adjacent two months and FIG. 18 shows a data graph for describing questionnaire score variation between adjacent two months. From the data of clinical trials provided in FIG. 17 and FIG. 18, it is further understood that, the adult men wearing the underpants provided by the present invention for three months have an apparent progress on improvements of their ejaculation control ability and lower urinary tract symptoms (LUTS), compared to the adult men wearing the underpants provided by the present invention for one month.

Second Clinical Trials

Second clinical trials are planned for verifying the accuracy of the data corrected from the first clinical trials. According to following Table (2), adult men not sure to suffer from sexual dysfunction are chosen as test subjects, and further divided into control group (abbreviated to group C) and experimental group (abbreviated to group E) for completing 3-month clinical trials. It needs to further explain that, both the adult men of the group C and the group E wear the underpants 1 provided by the present invention. Moreover, the primary difference between the group C and the group E is that the adult men of the group C has been informed that the underpants they wore is a commercial underpants. On the other hand, in Table (2), physiology examination reports to be "abnormal" means the adult men suffer from hypertension.

TABLE (2)

| | Physiology examination | | Age | | | BMI | | |
|---|---|---|---|---|---|---|---|---|
| | Normal | Abnormal | Avg. | ± | Standard deviation | Normal | Over weight | Obese |
| Group C (n = 5) | 4 | 1 | 46.66 | ± | 5.36 | 2 | 3 | 0 |
| Group E (n = 14) | 13 | 1 | 48.93 | ± | 7.45 | 2 | 8 | 4 |

Figure 19:
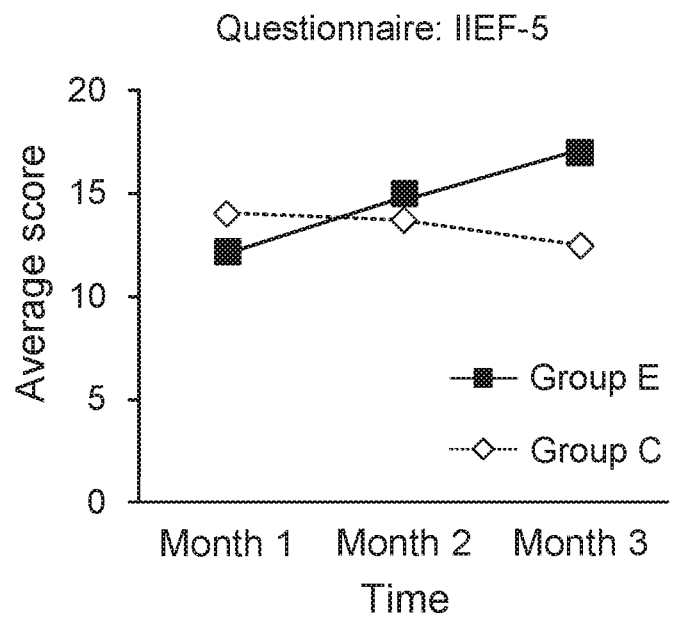
FIG. 19 shows a data graph of time of clinical experiment versus average score of questionnaire.
Figure 20:
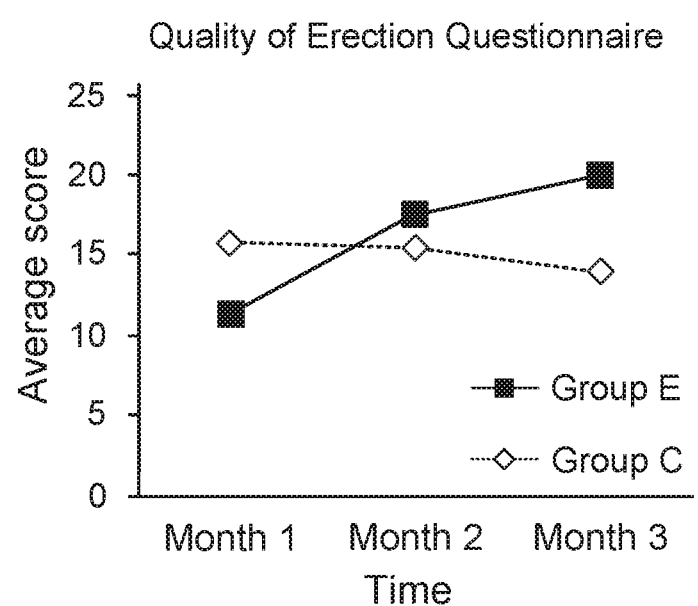
FIG. 20 shows a data graph of time of clinical experiment versus average score of questionnaire.
Figure 21:
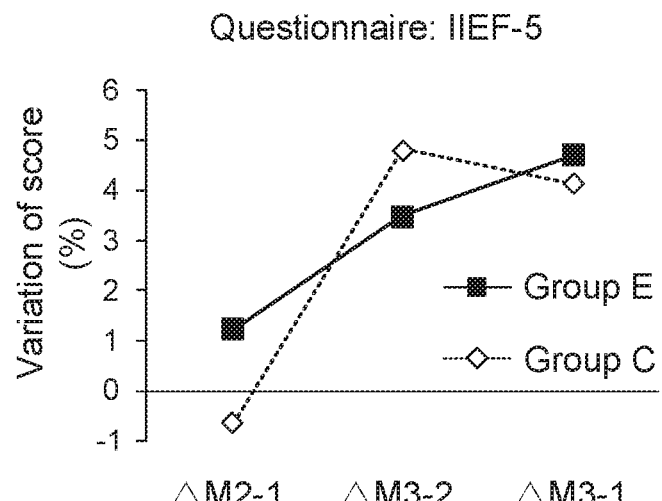
FIG. 21 shows a data graph for describing questionnaire score variation between adjacent two months.
Figure 22:
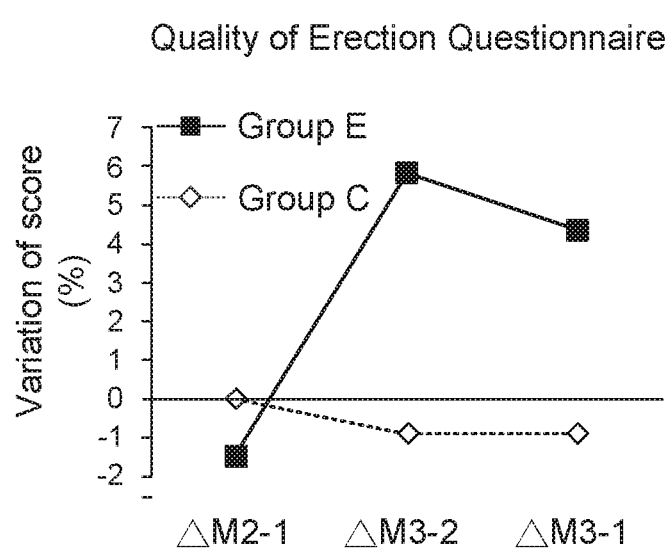
FIG. 22 shows a data graph for describing questionnaire score variation between adjacent two months.

During 3-month clinical trials, the test subjects are requested to come back for follow up at the hospital every 1 month for completing the filling of four questionnaires of IIEF-5, QEQ, PEDT, and IPSS. Moreover, physiological data of the test subjects are also measured and recorded by nursing personnel. Diagrams of IIEF-5 questionnaire, QEQ questionnaire, PEDT questionnaire, and IPSS questionnaire are displayed in FIG. 19, FIG. 20, FIG. 21, and FIG. 22, respectively. FIG. 19 shows a data graph of time of clinical experiment versus average score of questionnaire, and FIG. 20 shows a data graph of time of clinical experiment versus average score of questionnaire. From the data of clinical trials provided in FIG. 19 and FIG. 20, it is found that, compared to the adult men wearing the underpants provided by the present invention for one month, the adult men wearing the underpants provided by the present invention for three months have an apparent progress on improvements of their erectile ability and erectile quality. On the other hand, FIG. 21 shows a data graph for describing questionnaire score variation between adjacent two months and FIG. 22 shows a data graph for describing questionnaire score variation between adjacent two months. From the data of clinical trials provided in FIG. 21 and FIG. 22, it is further understood that, the adult men wearing the underpants provided by the present invention for three months have an apparent progress on improvements of their erectile ability and erectile quality, compared to the adult men wearing the underpants provided by the present invention for one month.

Figure 23:
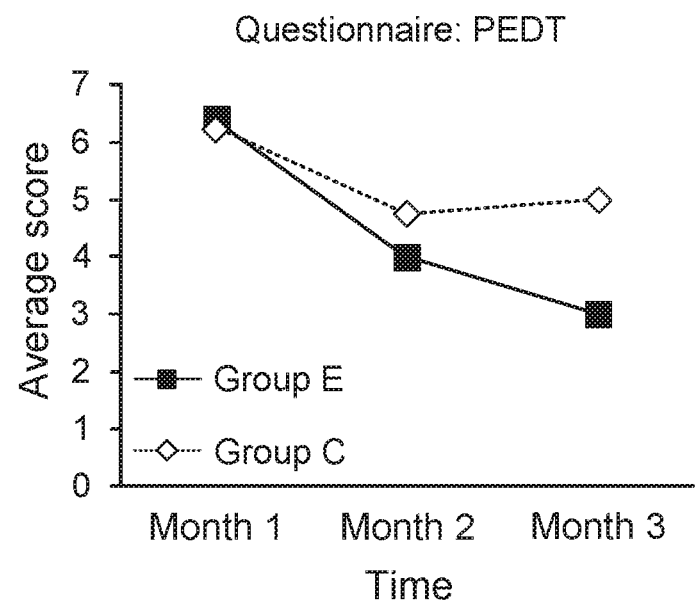
FIG. 23 shows a data graph of time of clinical experiment versus average score of questionnaire.
Figure 24:
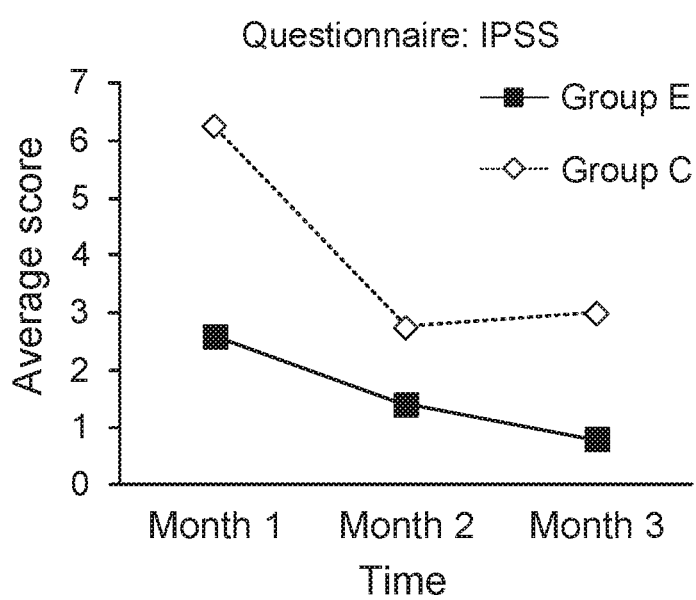
FIG. 24 shows a data graph of time of clinical experiment versus average score of questionnaire.
Figure 25:
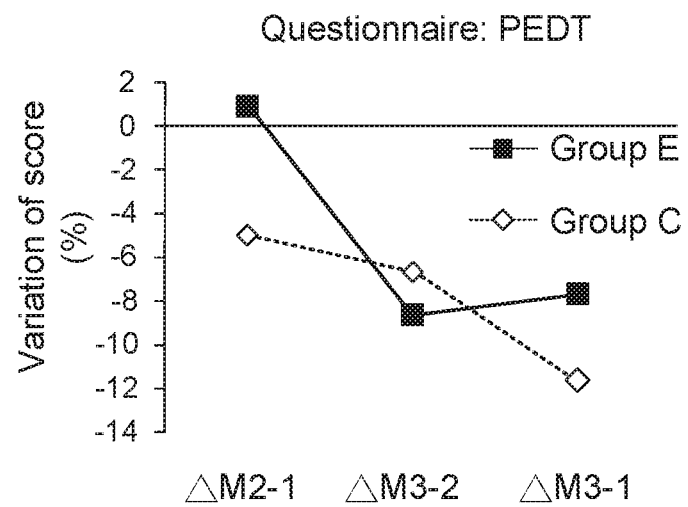
FIG. 25 shows a data graph for describing questionnaire score variation between adjacent two months.
Figure 26:
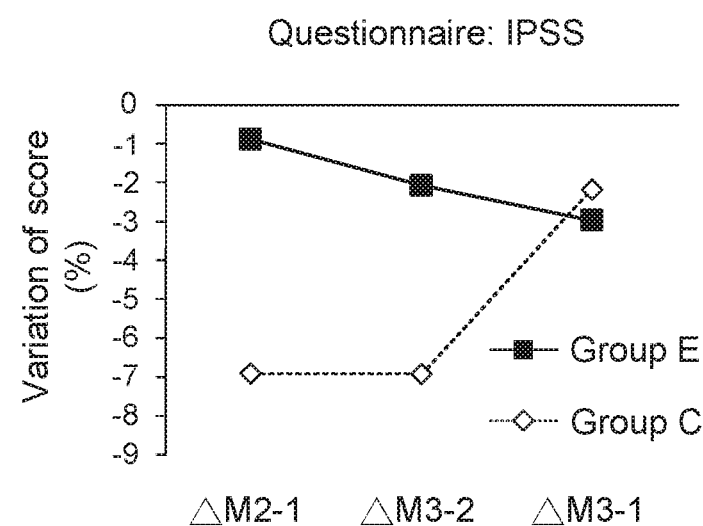
FIG. 26 shows a data graph for describing questionnaire score variation between adjacent two months.

In addition, FIG. 23 shows a data graph of time of clinical experiment versus average score of questionnaire, and FIG. 24 shows a data graph of time of clinical experiment versus average score of questionnaire. From the data of clinical trials provided in FIG. 23 and FIG. 24, it is found that, compared to the adult men wearing the underpants provided by the present invention for one month, the adult men wearing the underpants provided by the present invention for three months have an apparent progress on improvements of their ejaculation control ability and lower urinary tract symptoms (LUTS). On the other hand, FIG. 25 shows a data graph for describing questionnaire score variation between adjacent two months and FIG. 26 shows a data graph for describing questionnaire score variation between adjacent two months. From the data of clinical trials provided in FIG. 25 and FIG. 26, it is further understood that, the adult men wearing the underpants provided by the present invention for three months have an apparent progress on improvements of their ejaculation control ability and lower urinary tract symptoms (LUTS), compared to the adult men wearing the underpants provided by the present invention for one month.

Furthermore, data of FIG. 11-FIG. 26 are integrated in following Table (3) and Table (4).

TABLE (3)

| Questionnaire | Group C | | | | | | | |
|---|---|---|---|---|---|---|---|---|
| | First month | | Third month | | Improvement status | | | |
| | Avg. of score ± | Standard deviation | Avg. of score ± | Standard deviation | improved | unimproved | P value |
| IIEF-5 | 17.7 ± | 8.53 | 17.33 ± | 8.51 | | ✓ | 0.92 |
| QEQ | 19.30 ± | 8.46 | 18.11 ± | 8.34 | | ✓ | 0.76 |
| PEDT | 6.3 ± | 5.21 | 4.44 ± | 3.71 | ✓ | | 0.38 |
| IPSS | 8.00 ± | 10.72 | 6.00 ± | 8.00 | ✓ | | 0.64 |

TABLE (4)

| Questionnaire | Group C | | | | | | | |
|---|---|---|---|---|---|---|---|---|
| | First month | | Third month | | Improvement status | | | |
| | Avg. of score ± | Standard deviation | Avg. of score ± | Standard deviation | improved | unimproved | P value |
| IIEF-5 | 18.33 ± | 6.54 | 2026 ± | 5.69 | ✓ | | 0.33 |
| QEQ | 19.57 ± | 7.53 | 22.53 ± | 8.02 | ✓ | | 0.24 |
| PEDT | 5.14 ± | 4.22 | 3.16 ± | 3.76 | ✓ | | 0.12 |
| IPSS | 3.86 ± | 6.40 | 2.58 ± | 4.06 | ✓ | | 0.45 |

Therefore, data of clinical trials have proved that, after wearing the underpants provided by the present invention for three months, both the men diagnosed with sexual dysfunction and the men not sure to suffer from sexual dysfunction have an apparent progress on improvements of their erectile ability, erectile quality, ejaculation control ability, and lower urinary tract symptoms (LUTS).

It is worth explaining that, the far-infrared fibers 11 contained by the underpants 1 (as FIG. 5 shows) would emit electromagnetic radiation in the far infrared region (wavelength 4-14 microns). Such far-infrared rays have been examined for effects on human leukocyte activity and on lipid peroxidation of unsaturated fatty acids. Moreover, related research also report that far-infrared rays significantly increase intracellular calcium ion concentration, phagocytosis, and generation of reactive oxygen species in neutrophils, and the blastogenetic response of lymphocytes to mitogens. Despite the increase in reactive oxygen species generated by neutrophils, lipid peroxidation from unsaturated fatty acid may be markedly inhibited by far-infrared rays, related research suggest that the far-infrared rays can be widely used for cosmetic, therapeutic, and preservative purposes, appear capable of potentiating leukocyte functions without promoting oxidative injury. On the other hand, far-infrared ray (FIR) radiation has been proved to be beneficial to human health. Particularly, related research have investigated the effect carried out by FIR on the expression of calmodulin (Cam) protein and nitric oxide (NO) production in human body. Experimental data indicated a significant increase in Cam protein in FIR-treated RAW 264.7 macrophages with or without the addition of lipopolysaccharide (LPS). In addition, the amount of NO was slightly higher but increased significantly in FIR plus LPS-treated RAW 264.7 macrophages.

It is worth explaining that, the physiologic mechanism of erection of the penis involves release of nitric oxide (NO) in the corpus cavernosum during sexual stimulation. Related research indicates that NO would activate the enzyme guanylate cyclase, which results in increased levels of cyclic guanosine monophosphate (cGMP), so as to produce smooth muscle relaxation in the corpus cavernosum and allowing inflow of blood. NO in vascular regulation couples endothelial and smooth muscle cells. In blood vessels, vascular dilation is initiated by acetylcholine acting at muscarinic receptors on endothelial cells. This initiates IP3 production, $Ca^{2+}$ release from endoplasmic reticulum and activation of NO synthase by $Ca^{2+}$/calmodulin. Nitric oxide diffuses to smooth muscle cells and activates guanylyl cyclase. cGMP activates a cGMP-dependent protein kinase which phosphorylates myosin light chain and causes vascular relaxation.

It is repeated that, when an adult man wear this underpants 1 (as shown in FIG. 5), the far-infrared rays emitted from the front rise portion 13 and the crotch portion 14 of the underpants 1 would make the dilation of penile arteries of the adult man, and simultaneously urge blood to flow into the penile arteries so as to make the erection of the adult man's penis. Accordingly, physiological data of the test subjects measured by nursing personnel are integrated in following Table (5), Table (6) and Table (7). Therefore, the recorded physiological data have proved that, despite the fact that the adult men wear the underpants provided by the present invention for three months, there is no any adverse effect induced by the underpants so as to cause the physiological condition of the men be abnormal.

TABLE (5)

| physio-logical data | First month | | | |
|---|---|---|---|---|
| | Average | ± Standard deviation | Maximum | Minimum |
| SBP (mmHg) | 126.64 | ± 9.92 | 147.00 | 108.00 |
| DBP (mmHg) | 80.86 | ± 9.13 | 98.00 | 64.00 |
| Body Temp. (° C.) | 36.37 | ± 0.56 | 37.2 | 35.00 |
| Pulse (bit/min) | 73.29 | ± 7.25 | 93.00 | 64.00 |

TABLE (6)

| physio-logical data | Second month | | | |
|---|---|---|---|---|
| | Average | ± Standard deviation | Maximum | Minimum |
| SBP (mmHg) | 123.33 | ± 8.50 | 140.00 | 110.00 |
| DBP (mmHg) | 83.44 | ± 6.64 | 92.00 | 71.00 |
| Body Temp. (° C.) | 36.64 | ± 0.29 | 37.00 | 36.20 |
| Pulse (bit/min) | 74.44 | ± 8.23 | 96.00 | 64.00 |

TABLE (7)

| physio-logical data | Third month | | | |
|---|---|---|---|---|
| | Average | ± Standard deviation | Maximum | Minimum |
| SBP (mmHg) | 126.00 | ± 8.29 | 135.00 | 115.00 |
| DBP (mmHg) | 84.00 | ± 7.79 | 93.00 | 74.00 |
| Body Temp. (° C.) | 36.20 | ± 0.28 | 36.60 | 36.00 |
| Pulse (bit/min) | 73.67 | ± 12.12 | 90.00 | 61.00 |

Therefore, through above descriptions, the method for treating male sexual dysfunction by using underpants comprising far-infrared fibers proposed by the present invention have been introduced completely and clearly; in summary, the present invention includes the advantages of:

(1) Differing from conventional approaches for improving sexual dysfunction of an adult man being commonly carried out by letting the adult man administer a dosage of synthetic drug or a composition of Chinese herbal medicines, the present invention particularly discloses a method for treating male sexual dysfunction by using underpants comprising far-infrared fibers. A variety of clinical data have proved that, after wearing this underpants for three months, both the men diagnosed with sexual dysfunction and the men not sure to suffer from sexual dysfunction have an apparent progress on improvements of their erectile ability, erectile quality, ejaculation control ability, and lower urinary tract symptoms (LUTS).

(2) Moreover, clinical data have also proved that, despite the fact that a male person wears the underpants provided by the present invention for three months, there is no adverse effect induced by the underpants for causing the physiological condition of the men be abnormal.

The above description is made on embodiments of the present invention. However, the embodiments are not intended to limit scope of the present invention, and all equivalent implementations or alterations within the spirit of the present invention still fall within the scope of the present invention.

What is claimed is:

1. A method for treating male sexual dysfunction by using underpants comprising far-infrared fibers, comprising following steps:

(1) providing an underpants weaved from a plurality of far-infrared fibers and a plurality of fibers, wherein a crotch portion of the underpants is constituted by the far-infrared fibers such that the far-infrared fibers have a fiber amount that occupies 20-50 percent of a total fiber amount of the underpants; and wherein each of the plurality of far-infrared fibers comprises a polymer sheath and far-infrared powders that comprise powdered titanium (Ti) with a first metal weight percent of 18 wt %, powdered germanium (Ge) with a second metal weight percent of 0.2 wt % and powdered zinc (Zn) with a third metal weight percent of 0.15 wt % and is doped in or enclosed by the polymer sheath; and (2) letting adult men diagnosed with sexual dysfunction or not sure to suffer from sexual dysfunction wear the underpants for at least one month.

2. The method of claim 1, wherein the type of the underpants is selected from the group consisting of briefs, boxer briefs and boxer shorts.

3. The method of claim 1, wherein the manufacturing material of the polymer sheath is selected from the group consisting of polyester (PET), polyurethane (PU), Poly (vinyl chloride) (PVC), poly propylene (PP), and polyamide (PA).

4. The method of claim 1, wherein the polymer sheath is made of a polymer compound comprising silica of at least 50 wt %, and the chemical structure of the polymer compound is presented by following chemical formula 1:

[chemical formula 1]

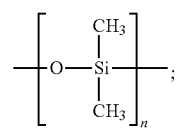

wherein n in the chemical formula 1 is in a range from 50 to 100.

5. The method of claim 1, wherein the far-infrared fibers are able to emit a far-infrared ray with a wavelength in a range from 2 μm to 22 μm, and the emissivity of the far-infrared ray is above 90%.

6. The method of claim 1, wherein the far-infrared powders further comprises powdered oxide and powdered carbide for increasing the emissivity of the far-infrared ray.

7. The method of claim 6, wherein the powdered oxide is selected from the group consisting of: $Al_2O_3$, $MgO$, $NiO_2$, $SiO_2$, $ZrO_2$, and a mixture made by any two or more aforesaid materials.

8. The method of claim 6, wherein the powdered carbide is selected from the group consisting of: $TaC$, $ZrC$, $SiC$, and a mixture made by any two or more aforesaid materials.

* * * * *